United States Patent
Bosnyak et al.

(10) Patent No.: US 9,212,273 B2
(45) Date of Patent: Dec. 15, 2015

(54) ELASTOMER FORMULATIONS

(75) Inventors: Clive P. Bosnyak, Dripping Springs, TX (US); Kurt W. Swogger, Austin, TX (US); Kenneth W. Hester, Gambsheim (FR)

(73) Assignee: Molecular Rebar Design, LLC, Austin, TX (US)

( * ) Notice: Subject to any disclaimer, the term of this patent is extended or adjusted under 35 U.S.C. 154(b) by 0 days.

(21) Appl. No.: 13/993,206

(22) PCT Filed: Dec. 12, 2011

(86) PCT No.: PCT/EP2011/072427
§ 371 (c)(1),
(2), (4) Date: Jun. 11, 2013

(87) PCT Pub. No.: WO2012/080160
PCT Pub. Date: Jun. 21, 2012

(65) Prior Publication Data
US 2013/0281612 A1    Oct. 24, 2013

Related U.S. Application Data

(60) Provisional application No. 61/423,033, filed on Dec. 14, 2010.

(30) Foreign Application Priority Data

Jun. 20, 2011 (WO) ................ PCT/US2011/041078

(51) Int. Cl.
| | | |
|---|---|---|
| C08K 3/04 | (2006.01) | |
| C08K 7/06 | (2006.01) | |
| C08K 7/24 | (2006.01) | |
| B60C 1/00 | (2006.01) | |
| C01B 31/02 | (2006.01) | |
| C08L 21/02 | (2006.01) | |
| C08K 7/08 | (2006.01) | |
| B82Y 30/00 | (2011.01) | |
| B82Y 40/00 | (2011.01) | |
| C08J 5/00 | (2006.01) | |
| C08L 9/10 | (2006.01) | |
| C08L 7/00 | (2006.01) | |
| C08L 9/06 | (2006.01) | |
| C08L 9/08 | (2006.01) | |
| C08K 5/42 | (2006.01) | |

(52) U.S. Cl.
CPC ... *C08K 7/08* (2013.01); *B60C 1/00* (2013.01); *B82Y 30/00* (2013.01); *B82Y 40/00* (2013.01); *C01B 31/022* (2013.01); *C01B 31/0273* (2013.01); *C08J 5/005* (2013.01); *C08K 3/04* (2013.01); *C08K 7/24* (2013.01); *C08L 9/10* (2013.01); *C08K 5/42* (2013.01); *C08K 2201/011* (2013.01); *C08L 7/00* (2013.01); *C08L 9/06* (2013.01); *C08L 9/08* (2013.01); *Y02T 10/862* (2013.01)

(58) Field of Classification Search
CPC ............. C08K 3/04; C08K 7/06; C08K 7/24; C01B 31/02; C01B 31/022; C01B 31/0206; B60C 1/00; C08L 21/02
USPC ................................................ 524/495, 575
See application file for complete search history.

(56) References Cited

U.S. PATENT DOCUMENTS

| | | | |
|---|---|---|---|
| 7,453,085 B2 | 11/2008 | Chang et al. | |
| 2007/0244263 A1 | 10/2007 | Burrowes | |
| 2007/0259994 A1 * | 11/2007 | Tour et al. ..................... | 523/333 |
| 2009/0169876 A1 | 7/2009 | Yamamoto et al. | |
| 2010/0258238 A1 | 10/2010 | Hoover et al. | |

FOREIGN PATENT DOCUMENTS

WO        WO 03060002 A1 *   7/2003

OTHER PUBLICATIONS

Sui et al. "Curing kinetics and mechanical behavior of natural rubber reinforced with pretreated carbon nanotubes", Materials Science and Engineering A, vol. 485, p. 524-531,2008.*
S. Bhattacharyya et al. "Improving reinforcement of natural rubber by networking of activated carbon nanotubes", Carbon 46 (2008), pp. 1037-1045.*
Chinese Patent Office; First Office Action; Chinese Application No. 201180065092.6; Aug. 26, 2014.
Chinese Patent Office; First Office Action (in English); Chinese Application No. 201180065092.6; Aug. 26, 2014.
Chinese Patent Office; First Office Action; Chinese Application No. 201180065089.4; Aug. 15, 2014.
Chinese Patent Office; First Office Action (in English); Chinese Application No. 201180065089.4; Aug. 15, 2014.
Chinese Patent Office; First Office Action; Chinese Application No. 201180067408.5; Nov. 2, 2014.
Chinese Patent Office; First Office Action (in English); Chinese Application No. 201180067408.5; Nov. 2, 2014.

* cited by examiner

*Primary Examiner* — Ling Choi
*Assistant Examiner* — Ronald Grinsted
(74) *Attorney, Agent, or Firm* — Gregory L. Porter; Andrews Kurth LLP

(57) ABSTRACT

This present invention relates to carbon nanotubes as fillers in composites with materials such as elastomers, thermosets and thermoplastics. A further feature of this invention relates to the development of a concentrate of carbon nanotubes with an elastomer wherein the concentrate can be further diluted with an elastomer and other polymers and fillers using conventional melt mixing.

14 Claims, 4 Drawing Sheets

ELASTOMER FORMULATIONS

This application claims priority to International Application No. PCT/EP2011/072427 filed Dec. 12, 2011; PCT Application No. PCT/US2011/041078 filed Jun. 20, 2011 and U.S. Provisional Application No. 61/423,033 filed Dec. 14, 2010, the entire contents of each are incorporated herein by reference.

FIELD OF INVENTION

The present invention is directed to novel compositions and methods for producing elastomer composite blends and elastomer materials with discrete carbon nanotubes.

BACKGROUND OF THE INVENTION

Carbon nanotubes can be classified by the number of walls in the tube, single-wall, double wall and multiwall. Each wall of a carbon nanotube can be further classified into chiral or non-chiral forms. Carbon nanotubes are currently manufactured as agglomerated nanotube balls or bundles.

It is desirable to use carbon nanotubes (also known as carbon nanotube fibres) as a reinforcing agent in elastomer composites. However, utilization of carbon nanotubes in these applications has been hampered by the general inability to reliably produce discrete or individualized carbon nanotubes. To reach the full potential of performance enhancement of carbon nanotubes as composites in elastomers the carbon nanotubes need to be separated. In this context one may also speak of exfoliated, debundled, disentangled or discrete nanotubes. All of these terms intended to describe individual nanotubes, i.e. nanotubes that are separated from other nanotubes.

Various methods have been developed to debundle or disentangle carbon nanotubes in solution. For example, carbon nanotubes may be shortened extensively by aggressive oxidative means and then dispersed as individual nanotubes in dilute solution. These tubes, however, are too short for use as reinforcing materials, especially in high strength composite materials.

Useful procedures to produce discrete nanotubes are disclosed in US 2011/0151321, WO 2010/117392 and Wang et al., Carbon 41 (2003) 2939. The entire disclosure of these references is hereby incorporated by reference.

SUMMARY OF THE INVENTION

It is the object of the present invention to utilise discrete carbon nanotubes in elastomer compositions.

The present inventors have found that discrete nanotubes can be used advantageously in elastomeric compositions, if the nanotubes are sufficiently separated. According to the present invention, carbon nanotubes are sufficiently separated for use in elastomeric compositions, if at least 70% of all nanotubes in the composition have an aspect ratio of more than 10. Such nanotubes are considered discrete nanotubes in the sense of the present invention.

In a first aspect, the present invention relates to compositions comprising a liquid phase and dispersed discrete nanotubes. Lattices obtained by mixing such compositions with elastomers are also considered in the present invention. In a second aspect, the present invention relates to mixtures comprising elastomers and discrete nanotubes and in a third aspect, the present invention relates to cured elastomers containing discrete nanotubes.

DETAILED DESCRIPTION OF THE INVENTION

While most of the terms used herein will be recognizable to those of ordinary skill in the art, it should be understood, however, that when not explicitly defined, terms should be interpreted as adopting a meaning presently accepted by those of ordinary skill in the art. In cases where the construction of a term would render it meaningless or essentially meaningless, the definition should be taken from Webster's Dictionary, 3rd Edition, 2009. Definitions and/or interpretations should not be incorporated from other patent applications, patents, or publications, related or not, unless specifically stated in this specification or if the incorporation is necessary for maintaining validity. The term "comprising" is to be construed as meaning both "consisting of" and "containing".

The present invention relates to compositions comprising a plurality of discrete carbon nanotubes having an aspect ratio of at least 10, preferably at least 40. The aspect ratio is preferably between 10 to 500, such as 25 to 500 or 40 to 500. Most preferred is an aspect ratio of 60 to 200.

Discrete nanotubes in the embodiments according to the present invention amount to at least 70% of all nanotubes. Preferably, the discrete nanotubes amount to at least 80 or even 90 wt.-%, most preferably 95% or 99% or more. These percentages can be determined by centrifugation or microscopy. If determined by centrifugation, it is convenient to use the weight fraction, i.e. percent based on weight of all nanotubes. In case of using centrifugation it may be more convenient to use the volume fraction, i.e. volume percent passed on volume of all nanotubes. However, as the volume fraction and the weight fraction is the same, either basis can be used, while the result is the same.

The aspect ratio as used in the present invention is the ratio of the length to the diameter of a nanotube or in case nanotubes are agglomerated, the aspect ratio is the ratio of the length to the diameter of the entire agglomerate. The aspect ratio is determined as the average length divided by the average diameter. The average is the arithmetic average. The maximum aspect ratio for a given tube length is reached when each tube is fully separated from another. A bundle of carbon nanotubes has an effective aspect ratio in composites of the average length of the bundle divided by the bundle diameter.

Figure 1:
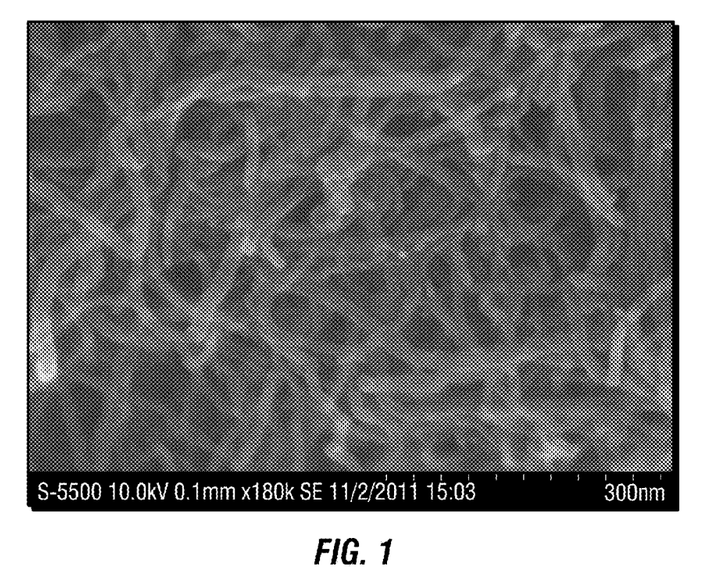
FIG. 1 is an SEM that shows nanotubes.

One suitable method to measure the diameters of the separated and agglomerated carbon nanotubes is scanning electron microscopy (SEM). The carbon nanotubes are deposited on a carbon tape and an image is taken at a suitable magnification such as 100,000 to 200,000×. An example for such a micrograph is shown in FIG. 1. Cords are constructed across the entire micrograph and the tube diameters are measured from those tubes intercepting the cords. At least 20 determinations are made.

Figure 2:
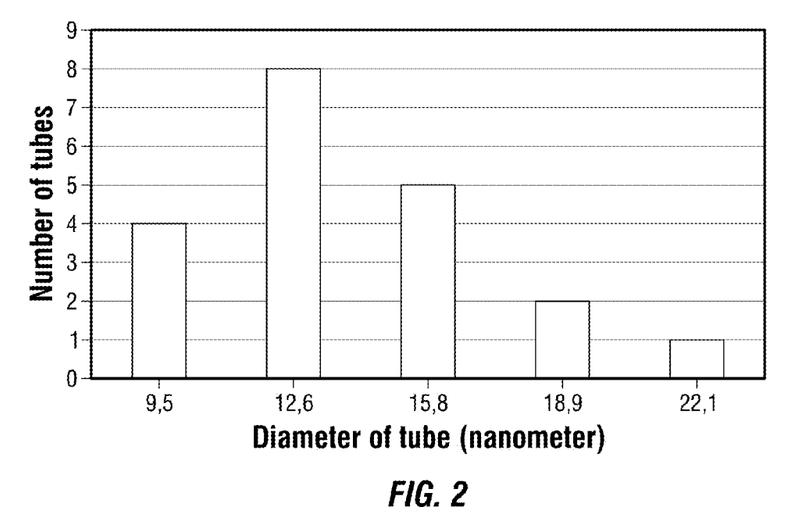
FIG. 2 is a histogram showing the number of nanotubes vs. diameter of the nanotubes.

On the basis of this measurement, a histogram can be constructed showing the diameter of the nanotubes on the x-axis and the number of nanotubes with the respective diameter on the y-axis. An example of such a histogram is shown in FIG. 2. In this specific determination the average diameter was calculated as 13.9 nm with a standard deviation of 3.5 nm.

Figure 3:
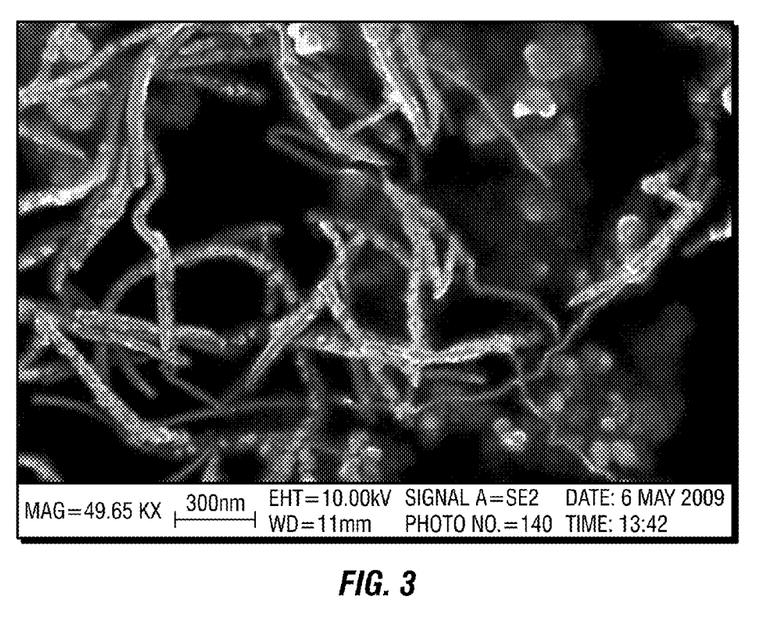
FIG. 3 is an SEM that shows discrete nanotubes, i.e., individual nanotubes that have been disentangled and separated from other nanotubes.
Figure 4:
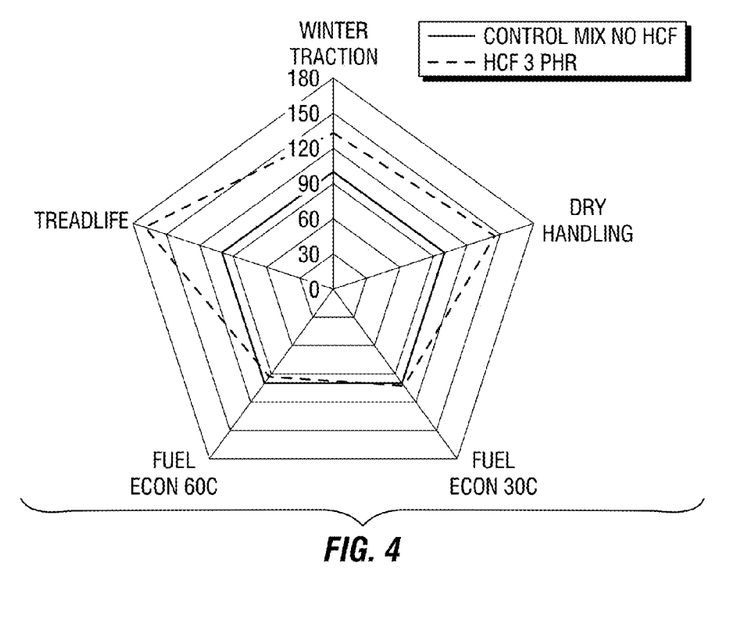
FIG. 4 is a comparison that shows tire tread properties for a control formulation and an HCF formulation.

The lengths of the tubes can also be measured using SEM. A dilute solution ($1\times10^{-6}$ g/ml) of carbon nanotubes is made in water containing a surfactant (e.g. dodecylbenzene sulfonic acid or a salt thereof). A drop of the dilute solution is placed on a carbon tape and dried. An image is taken under the conditions set forth above. The lengths are then measured for a sufficient number of nanotubes so as to obtain a measurement representative of the average. In practice, 5 to 10, preferably 20 or more measurements are taken. In the example of FIG. 3, seven complete tubes have been measured. The average length of the measured separated carbon nanotubes in this example is 776 nm with a standard deviation of 300 nm. As a result, the aspect ratio in this case is (776 nm/13.9 nm) 56.

The nanotube fibers according to the present invention may be further functionalized. Functionalized carbon nanotubes of the present invention generally refer to the chemical modification of any of the carbon nanotube types described hereinabove. Such modifications can involve the nanotube ends, sidewalls, or both. Chemical modifications may include, but are not limited to covalent bonding, ionic bonding, chemisorption, intercalation, surfactant interactions, polymer wrapping, cutting, solvation, and combinations thereof. In some embodiments, the carbon nanotubes may be functionalized before, during and after being separated.

The carbon nanotubes may be single wall, double wall or multi wall carbon nanotubes.

The carbon nanotubes may be partially oxidised. Specifically, they may be oxidised to an oxidation level of from about 2.5 weight percent to about 15 weight percent, preferably from about 3 to 15 or more preferably from about 5 weight percent to about 10 weight percent based on the total weight of the discrete nanotubes. The oxidation level is defined as the amount by weight of oxygenated species covalently bound to the carbon nanotube.

The degree of oxidation can be determined thermogravimetrically. The thermogravimetric method for the determination of the percent weight of oxygenated species on the carbon nanotube involves taking about 5 mg of the dried oxidized carbon nanotube and heating at 5° C./minute from room temperature to 1000 degrees centigrade in a dry nitrogen atmosphere. The percentage weight loss from 200 to 600 degrees centigrade is taken as the percent weight loss of oxygenated species. The oxygenated species can also be quantified using Fourier transform infra-red spectroscopy, FTIR, particularly in the wavelength range 1730-1680 $cm^{-1}$.

The carbon nanotube can be functionalized with oxidation species comprising of carboxylic acid or derivative carbonyl containing. The derivative carbonyl species can include ketones, further derivative species are quaternary amines, amides, esters, acryl halogens, monovalent metal salts and the like.

As-made carbon nanotubes using metal catalysts such as iron, aluminium or cobalt can retain a significant amount of the catalyst associated or entrapped within the carbon nanotube, as much as five weight percent or more. These residual metals can be deleterious in such applications as electronic devices because of enhanced corrosion or can interfere with the vulcanization process in curing elastomer composites. Furthermore, these divalent or multivalent metal ions can associate with carboxylic acid groups on the carbon nanotube and interfere with the discretization of the carbon nanotubes in subsequent dispersion processes. The oxidized nanotubes preferably comprise a residual metal concentration of less than about 10,000 parts per million (ppm) and preferably less than about 1,000 parts per million. The metals can be conveniently determined using energy dispersive X-ray, EDX.

The present invention relates to compositions comprising the above described carbon nanotubes and a liquid phase. The liquid phase may be aqueous or organic. The concentration ranges of the discrete carbon nanotubes in the liquid phase are from 0.1 to 5% by weight, preferably 0.5 to 3% by weight and most preferably 1 to 2% by weight.

For an aqueous solution, it is preferable to have a pH which is alkaline, i.e. higher than pH 7, so that the nanotubes are dispersed more easily; where most preferably it is within a range of 8 to 11.

The composition may further comprise at least one surfactant or dispersing aid. Illustrative surfactants used for dispersing carbon nanotubes in aqueous solution include, for example, sodium dodecyl sulfate, sodium dodecyl benzene sulfonate, polyethers, especially block polyethers, or cetyltrimethyl ammonium bromide.

The above composition comprising carbon nanotubes and a liquid phase can be used for mixing with an elastomer, such as a latex dispersion. Preferably, the weight ratio of carbon nanotubes to the elastomer is within the range of 0.01:0.99 to 0.3:0.7.

The elastomer in the sense of the present invention includes rubber polymers that may be subjected to curing. The elastomer can be a natural or a synthetic elastomer selected from the group consisting of, but not limited to, natural rubbers, polyisobutylene, polybutadiene and styrene-butadiene rubber, butyl rubber, polyisoprene, styrene-isoprene rubbers, ethylene propylenediene rubbers, silicones, polyurethanes, polyester-polyethers, hydrogenated and non-hydrogenated nitrile rubbers, halogen modified elastomers, fluoro-elastomers, and combinations thereof. The composition contains nanotubes as described above that are not entangled as a mass and are uniformly dispersed in the elastomer.

In the case of some elastomers, such as polybutadiene, styrene-butadiene rubber and nitrile rubbers, it may be preferable to use an organic solvent capable of dissolving the elastomer so as to form a dispersion of discrete nanotubes in a liquid phase. The liquid phase comprises the organic solvent and the elastomer. The concentrations of dispersed carbon nanotubes are preferably in the range 0.1 to 30% by weight of the mixture. Solvents useful for dissolution of the elastomers include hydrocarbons such as cyclohexane and n-heptane, aromatic solvents such as toluene and xylene, and polar solvents including N,N-dimethylformamide and N-methyl-2-pyrrolidone.

The above composition and latex may be obtained by a process comprising the following steps:
(a) selecting discrete carbon nanotubes as described above,
(b) blending the nanotubes with a liquid to form a liquid/nanotube mixture,
(c) optionally adjusting the pH to a desired level,
(d) agitating the mixture to a degree sufficient to disperse the nanotubes to form a dispersed nanotube mixture, (e) optionally combining the dispersed nanotube mixture with at least one surfactant, (f) combining the dispersed nanotube mixture with at least one elastomer at a temperature sufficient to incorporate the dispersed nanotubes mixture to form a carbon nanotube/elastomer composite/liquid mixture, (g) isolating the resulting carbon nanotube/elastomer composite from the liquid.

The carbon nanotube fibers comprise from about 0.1 to about 30, preferably 1 to 30, 10 to 25 or 15 to 20 weight percent of the fiber/elastomer composite of (g). The agitation in step (d) may comprise sonication.

In yet another embodiment of the invention is a carbon nanotube fiber/elastomer composite, wherein the carbon nanotube fibers are discrete fibers and comprise from about 10 to about 20 weight percent fibers and wherein the elastomer comprises a styrene copolymer rubber.

Isolation in step (g) may mean coagulation or evaporation of the solvent.

In a preferred embodiment of the invention the method for obtaining individually dispersed carbon nanotubes in rubbers and/or elastomers comprises the steps of:

(a) forming a solution of exfoliated carbon nanotubes at pH greater than or equal to about 7,
(b) adding the solution to a rubber or elastomer latex to form a mixture at pH greater than or equal to about 7,
(c) coagulating the mixture to form a concentrate,
(d) optionally incorporating other fillers and or an antioxidant into the concentrate and
(e) optionally melt-mixing said concentrate into rubbers and/or elastomers to form elastomeric concentrate, composites.

In this embodiment the carbon nanotubes preferably comprise less than or equal to about 30 percent by weight of the solution, at various desired levels such as 20 or 10 percent and a most preferred level of less than or equal to 2 percent by weight of the solution.

In a preferred embodiment the coagulation step in the above methods comprises mixing with acetone. In another embodiment, the coagulation step comprises drying the mixture. In yet another embodiment the coagulation step comprises adding at least one acid to the mixture at a pH less than or equal to about 4.5 together with at least one monovalent inorganic salt.

Another aspect of this invention are coagulating methods/agents that enable the carbon nanotube to be non-ordered on the surface of the elastomer latex particle and together are substantially removable from the liquid mixture.

A further aspect of this invention is a method to reduce or remove surfactants in the latex/carbon nanotube fiber composite system with organic molecules of high water solubility such as acetone, denatured alcohol, ethyl alcohol, methanol, acetic acid, tetrahydrofuran.

Another aspect of this invention is to select coagulating methods that retain surfactant in the latex/carbon nanotube fiber material which includes coagulating methods such as sulfuric acid and inorganic monovalent element salt mixtures, acetic acid and monovalent element salt mixtures, formic acid and inorganic monovalent element salt mixtures, air drying, air spraying, steam stripping and high speed mechanical agitation.

In a preferred embodiment for aqueous elastomeric dispersions, the present invention excludes salts, acetone and/or other organic solvents in the coagulation addition step. In this embodiment, it is further preferable to use acids, bases and organic coagulation aids to produce the carbon nanotube/elastomer composite.

At the start of this preferred embodiment of the process, the carbon nanotube dispersion and the aqueous elastomer dispersion or dispersions are blended together. The pH of the resulting dispersion blend should be greater than 8 and preferably greater than 10. The pH can be increased as required using bases such as sodium or ammonium hydroxide, most preferably sodium hydroxide.

One may then add a flocculent such as casein, polyamide, polyacrylamide, polyethyleneimine, cation modified starch, dicynodiamide-formaldehyde condensation product, or, most preferably, cationic polyamine.

Subsequently, one may add an acid such as acetic acid, hydrochloric acid, most preferably sulfuric acid whilst agitating. In this way, one preferably lowers the pH to less than 4, preferably less than pH 2.0, followed by isolating the resulting carbon nanotube/elastomer composite from the liquid.

The above steps in the preferred embodiment may be undertaken at room or elevated temperatures, preferably in the range of 60 to 80° C.

The advantage of this process is that it is salt free and specifically excludes the acetone/organic solvent step which is more costly on capital than the process described here well as reducing waste stream management to a purely aqueous, low salinity, waste water stream. The embodiment also limits the amount of salt derived ash in the composite.

In another aspect, the isolated mixture may have a divalent or multivalent metal ion content of less than about 20,000 parts per million, preferably less than about 10,000 parts per million and most preferably less than about 1,000 parts per million.

The invention also relates to a nanotubes/elastomer composite further comprising of filler or fillers such as carbon black and/or silica. The molded film comprising the composition may have a tensile modulus at 5 percent strain of at least about 12 MPa. The composition comprising of carbon black, and wherein a molded film comprising the composition may have a tear property of at least about 0.8 MPa. The invention also relates to a carbon nanotube/elastomer composition comprising a filler, and wherein a molded film comprising the composition has a tensile modulus at 5% strain of at least 8 MPa.

Yet another aspect of the invention is an individually dispersed carbon nanotube/rubber or carbon nanotube elastomer concentrate comprising free flowing particles or a bale. The concentrate preferably contains a concentration of less than 20,000 parts per million of a divalent or multivalent metal salt. In such concentrate, agglomerations of carbon nanotubes should be avoided as much as possible. However, agglomerates that comprise less than 1 percent by weight of the concentrate and wherein the carbon nanotube agglomerates comprise more than 10 microns in diameter can be tolerated.

The elastomer nanotube fiber composition, particularly materials may be made from elastomers commnonly called either natural or synthetic rubber or rubber compounds (with the addition of fillers such as carbon or silica) includes wherein the nanotube surface modifier or surfactant is chemically or physically (or both) bonded to the elastomer and/or the isolated fibers or the filler in the compounds. As an example, oleylamine (1-amino-9-octadecene) can be reacted with carbon nanotubes containing carboxylic groups to give the amide. On addition of the amide modified carbon nanotube to a vinyl containing polymer material such as styrene-butadiene followed by addition of crosslinking agents comprising such as peroxides or sulfur, the vinyl containing polymer can be covalently bonded to the amide functionality of the carbon nanotube.

The elastomer/carbon nanotube concentrate may be dispersed first into another elastomer or thermoplastic polymer to a uniform consistency before addition of other additives such as other fi unif and additives, including carbon black, silica, graphene, oils and antioxidants. Antioxidants can be selected from benzimidazole, bisphenol, dihydrocholine, diphenylamine, monophenol, naphthylamine, p-phenylne diamine and derivatives thereof. Typical primary antioxidants are hindered phenolics such as 2,6-di-t-butylhydroxytoluene and hindered aromatic amines such as N,N'-dialkyldiphenylamines. Examples of secondary antioxidants are organic phosphites esters such as tris(nonyl-phenol)phosphite and sulfides or thioesters. These additives, and possibly others such as plasticizing oils and optionally surfactants can be added to the dispersion of discrete carbon nanotubes and/or latex. Optionally these additives can be added to the coagulated elastomer carbon nanotube crumb, for example via spraying or added during melt mixing of the elastomer or elastomers and discrete carbon nanotubes.

Another embodiment of this invention is a method of mixing carbon nanotubes and at least one first elastomer so as to obtain a master batch. Said master batch of carbon nanotubes may then be first melt mixed with a further elastomer, which may be either the same or different from the first elastomer, at a temperature from about 20 to about 200° C., subsequently then additional elastomers, fillers, and additives are added and melt mixed further, to produce a composition suitable for vulcanization.

A solvent can be added to facilitate mixing which can be removed before, during or after the at least one first elastomer, wherein a master batch of carbon nanotubes is first mixed with the elastomer, or after all ingredients are added and mixed. Normally the mixing time does not exceed one hour and a time in the range from 2 to 30 minutes is usually adequate. The temperature is usually between 20° C. and 200° C.

The mixing is suitably carried out in a blending apparatus, e.g. an internal mixer such as a Banbury mixer, or a Haake or Brabender miniature internal mixer. A two roll mill mixer also provides a good dispersion of the carbon-nanotubes as well as of the other optional additives within the elastomer. An extruder also provides good mixing, and permits shorter mixing times. It is possible to carry out the mixing in one or more stages, and the mixing can be done in different apparatus, for example one stage in an internal mixer and one stage in an extruder. However, it should be taken care that no unwanted pre-crosslinking (scorch) occurs during the mixing stage.

In another embodiment, a mixture of master batches using different rubbers may be added to blends of different rubbers used in the rubber compound such that each rubber has a master batch that is compatible so that the individually dispersed nanotubes are distributed whether uniformly or non-uniformly in each rubber domain. This is sometimes necessary so that blends of rubbers used in the rubber compound will have carbon nanotubes in each rubber component.

In another aspect, the invention relates to a formulation in the form of a molded or fabricated article, such as a tire, a gum chafer, a tire sidewall, a tire tread or casing, a hose, a belt, a seal, an automotive anti-vibration part, a windshield wiper blade, and a tank track pad, wheel, bushings or backer plate components. Preferred embodiments are tires for industrial, commercial, off-road and passenger car applications. They are typically made from rubber (both synthetic and natural) with reinforcing fillers (typically carbon black and silica). The fillers are added to improve the overall mechanical properties. Incorporation of the discrete nanotubes into such tires allows for the reduction of reinforcing fillers. Generally speaking, the reduction in reinforcing fillers as compared to the addition of discrete Nanotubes that may be achieved is greater than 1:1 and is most preferably above 2:1. The amount of reinforcing fillers used in traditional tire treads without discrete nanotubes is typically in the range of 30 to 150 phr, preferably between 50 and 90 phr total filler. In a most preferred embodiment, the tire has a tread wherein the concentration of discrete nanotubes is in the range of 0.7 vol. % and 30 vol. % and a concentration of reinforcing filler in the range of 0 to 30 vol. %.

The separated carbon nanotube fibers of this invention impart significant strength and stiffness to the materials. These new elastomer nanotube filler materials can improve the frictional, adhesive, cohesive, noise and vibration, rolling resistance, tear, wear, fatigue and crack resistance, hysteresis, large strain effects (Mullins effect), small strain effects (Payne effect) and oscillation or frequency properties and swelling resistance to oil of the elastomers and elastomer compounds. This change in properties will be beneficial for applications such as tires or other fabricated rubber or rubber compounded parts. It will also have further benefits in terms of sustainability such as lower emissions in overall tire manufacturing, better fuel economy due to enhanced properties, and less tires in the landfills due to extended tire lifetimes.

A carbon nanotube/elastomer composite according to the invention, exhibits improved resistance to creep under load and a slower rate of strain recovery after load by at least 10% compared to similar elastomer composites without discrete carbon nanotubes. The invention thus meets the need for improved green strength in profile extrusions of rubber goods such as grooved belts, wiper blades, and improved dimensional tolerances in moulded goods. For profile extrusions green strength is the resistance to deformation after exiting the die and before significant crosslinking has occurred to retain the shape. A measure of green strength is the resistance to flow under load, i.e. creep. Creep is determined by applying a constant load to a specimen and measuring the deformation with time. In molded rubber goods, particularly with complex shapes, it is desirable to maintain good dimensional tolerances. The present invention allows improved dimensional tolerances due to less strain recovery upon release of the mold pressure.

The compounding and vulcanization (curing) may be performed as known to any artisan (see e.g. Encyclopedia of Polymer Science and Engineering, Vol. 4, p. 66 et seq. (Compounding) and Vol. 17, p. 666 et seq. (Vulcanization)). Typically such vulcanization is performed at a temperature in the range of from 100 to 200° C., preferably 130 to 180° C. In one embodiment the preparation of a polymer vulcanizate comprises subjecting the inventive composition to a vulcanization during fabrication and/or form fixing such as injection or extrusion molding.

The following examples illustrate the present invention. Elements of the examples can and should be construed within the specific context of the example but also within the general framework of the present disclosure.

Example 1

Illustrative Process for Producing Discrete Oxidized Carbon Nanotubes 3 liters of sulfuric acid, 97 percent sulfuric acid and 3 percent water, and 1 liter of concentrated nitric acid containing 70 percent nitric acid and 3 percent water, are added into a 10 liter temperature controlled reaction vessel fitted with a sonicator and stirrer. 40 grams of non-discrete carbon nanotubes, grade Flowtube 9000 from CNano corporation, are loaded into the reactor vessel while stirring the acid mixture and the temperature maintained at 30° C. The sonicator power is set at 130-150 watts and the reaction is continued for three hours.

After 3 hours the viscous solution is transferred to a filter with a 5 micron filter mesh and much of the acid mixture removed by filtering using a 100 psi pressure.

The filter cake is washed one time with four liters of deionized water followed by one wash of four liters of an ammonium hydroxide solution at pH greater than 9 and then two more washes with four liters of deionized water. The resultant pH of the final wash is 4.5.

A small sample of the filter cake is dried in vacuum at 100° C. for four hours and a thermogravimetric analysis taken as described previously. The amount of oxidized species on the fiber is 8 percent weight and the average aspect ratio as determined by scanning electron microscopy is 60.

Example 2

Illustrative Method for Making a Dispersion of Discrete Nanotubes

The discrete oxidized carbon nanotubes (CNT) obtained in Example 1 are added in wet form to water to form a concentration by weight of 1 percent and the pH is adjusted to 9 using ammonium hydroxide. Sodium dodecylbenzene sulfonic acid and is added at a concentration 1.25 times the mass of oxidized carbon nanotubes. The solution is sonicated while stirring until the CNT's are fully dispersed in the solution.

Full dispersion of individual tubes is defined when the UV absorption at 500 nm is above 1.2 absorption units (an absorbance unit is defined as $A_\lambda = \log_{10}(I_o/I)$, wherein $A_\lambda$ is the absorbance at wavelength $\lambda$, $I_o$ is the intensity of the light before entering the sample and I is the intensity of the light after passing through the sample) for a concentration of $2.5 \times 10^{-5}$ g CNT/ml (compared to the same composition without nanotubes).

Example 3

Illustrative Example for Making a Dispersion and Coagulation

The discrete oxidized carbon nanotubes (CNT) in wet form are added to water to form a concentration by weight of 1 percent and the pH is adjusted to 9 using ammonium hydroxide. Sodium dodecylbenzene sulfonic acid and is added at a concentration 1.25 times the mass of oxidized carbon nanotubes. The solution is sonicated while stirring until the CNT are fully dispersed in the solution. Full dispersion of individual tubes is defined when the UV absorption at 500 nm is above 1.2 absorption units for a concentration of $2.5 \times 10^{-5}$ g CNT/ml.

Latex SBR LPF 5356 (Goodyear Rubber Company) with a solids SBR concentration of 70.2% (by weight) was added to the CNT solution such that the solids ratio is 10 parts CNT for 90 parts SBR by weight.

Sulfuric acid is then added sufficient to bring the pH to 2 and sodium chloride added at a ratio of 50 g/liter of fluid while stirring. Stirring continues for 10 minutes then the coagulant is removed by filtering. The filtrate is a clear liquid. The coagulant is dried in a vacuum oven at 40° C. overnight.

Example 4

Illustrative Method for Making an Elastomer Composition

Latex SBR LPF 5356 (Goodyear Rubber Company) with a solids SBR concentration of 70.2% (by weight) was added to the CNT dispersion of Example 2 such that the solids ratio is 10 parts CNT for 90 parts ESBR by weight.

Sulfuric acid is then added in sufficient quantities to bring the pH to 2 and sodium chloride added at a ratio of 50 g/liter of fluid while stirring. Stirring continues for 10 minutes then the coagulant is removed by filtering. The filtrate is a clear liquid. The coagulant is dried in a vacuum oven at 40° C. overnight.

Example 5

Comparative Test

An SBR concentrate is melt mixed with additional SBR (Lanxess VSL-5052-OHM) to give a final CNT concentration of 2 percent weight in a Brabender mixer by the following procedure. The temperature of the barrel is set to 115° C. The SBR and master batch are introduced into the barrel at a speed of 20-30 rpm. The speed is then increased to 50 rpm. Barrel temperature should reach 125° C. When the torque has reached a constant value, the speed is decreased to 5 rpm and the temperature controller is turned off. When the temperature in the barrel is 95° C., the speed is increased to 50 rpm. The cure package is added and mixing continues for 5 minutes. The cure package consists of sulfur 3.5 parts per hundred resin, phr, tetrabutylbenzothiozolsulfonamide 0.75 phr, diphenyl-guanidine 0.5 phr, stearic acid 1.5 phr, N-(1,3 Dimethylbutyl) N'-phenyl-p-phenyldiamine 2 phr and zinc oxide 3 phr.

A comparative 1 is made as above with the exception that no SBR concentrate is added.

The mixture is then cured under the following procedure using a compression molder. The platten temperature is set to 160° C., the curing overall time to 20 minutes and the water cooling time to 5 minutes. A mass of 40.6 g of rubber sample is cut into small ¼" pieces and placed in the center of mold window such that it forms a square, occupying ⅔ of the space. Foil sheets are used between sample and compression plates. Mold release is only used on the mold frame. The sample is compressed with pressure less than 10 psi for 2 minutes. Then, the pressure is increased to 25 tons and kept constant for the remaining curing cycle.

After curing the films are tested in tension at 25° C. using a tensile tester with an initial strain rate of $1 \times 10^{-2}$ area of the specimen. Strain is defined as the distance traversed by the crosshead of the instrument divided by the initial distance between the grips. The 100% modulus is that value of tensile stress at 100% strain. The films are also tested for work done to completely tear the specimen by introducing a razor edge notch of dimension one half width and perpendicular to the length of the specimen to a tensile specimen.

TABLE 1

Tensile properties of cured SBR without carbon nanotubes and SBR with discrete carbon nanotubes

| Sample | Tensile Strength (MPa) | 100% Modulus (MPa) | Work done to Tear (MPa) |
| --- | --- | --- | --- |
| SBR | 1.1 | 0.51 | 0.46 |
| SBR + 2 wt.-% CNT | 2.26 | 0.8 | 0.79 |

Table 1 shows significant improvements in the values of tensile strength, 100% modulus and work done to tear are gained using 2 percent weight of the carbon nanotubes of this invention. These attributes are important elements that lead to improved wear in elastomer composites.

Example 6

Preferred Mixing

Another aspect of this invention is a preferred method of mixing that results in improved properties wherein the master batch of carbon nanotubes is first melt mixed with another elastomer then additional rubbers, fillers and additives are added and melt mixed further to produce a composition suitable for vulcanization. Following is an example of preferred mixing A comparative example 5 is produced using 3 phr carbon nanotubes of this invention, and carbon black filled rubber system consisting of 3 melt passes. The first pass was to mix the rubber components 60 phr styrene butadiene, SBR Lanxess VSI,-5025-OHM and 40 phr Natural Rubber CB 60 grade, and an SBR-carbon nanotubes master batch containing 10 weight percent carbon nanotubes at about 160° C. The second pass was to mix into the first pass products 50 phr carbon black, type N330, 5 phr processing oil Sundex 8125, 1 phr antioxidant 6 PPD Santoflex, 3 phr zinc oxide and 3 phr stearic acid at about 160° C. The third pass was to mix in the sulfur curing compounds 1.5 phr sulfur and 1.3 phr TBBS at about 110° C. Each pass was performed with a fill factor of 75% using a Brabender mixer.

Example 5 is produced as follows. The improved mixing approach is the same as the control except the first pass is mixing the SBR with the carbon nanotubes master batch for 5 minutes at about 170° C. and followed by adding the natural rubber at about 160° C. and melt mixing for a further 5 minutes.

The results of testing the materials after curing for 8 minutes at about 160° C. are provided in Table 2. The rear initiation and total tear energy are determined from tear specimen ASTM D624-C.

TABLE 2

Results for Example 6

|  | Comparative | Invention |
|---|---|---|
| Tensile Stress at Break (MPa) | 18.8 | 20.6 |
| Tensile Elongation to Break % | 500 | 520 |
| Tear Initiation Energy (MPa) | 2.9 | 3.7 |
| Total Tear Energy (MPa) | 3.3 | 4.2 |

The above table 2 shows that the example of the invention (pre-diluted master batch with specific mixing) obtains improved tensile stress at break at over 1.7 MPa, improved tear initiation energy at over 0.7 MPa and including improved total tear energy at over 0.8 MPa versus the comparative example comprising different mixing techniques, proving the utility and inventiveness of the compositions of the invention.

Example 7

One benefit of the present invention is an improved green strength for profile extrusion of rubber goods. This can be illustrated as follows:

A styrene-butadiene rubber (Lanxess 5025) was mixed with a master batch of latex emulsion SBR (Styron 1500) and 15% wt oxidized carbon nanotubes in a Haake Lab mixer at 150 C for 10 minutes to give a composition containing 3 phr carbon nanotube (example A).

A control was made as example A except without carbon nanotubes.

A disc was made by compression molding at 110° C. of dimensions 4 mm thick and diameter 1.25 cm. Using a DMA Q 800 a load of 0.05 MPa was placed on the disc at 28° C. and the strain in compression determined as a function of time for 10 minutes. The specimen was then unloaded and the strain recovery recorded for a further 20 minutes.

In table 1 is recorded the applied stress for 10 minutes, the peak strain recorded at the end of 10 minutes and the percentage of strain recovered on unloading and after 20 minutes.

TABLE 3

Results for Example 7

| Sample | Applied Stress [MPa] | Peak Strain after 10 min | Strain Recovery after 20 min |
|---|---|---|---|
| Control | 0.05 | 0.189 | 87% |
| Invention | 0.05 | 0.0526 | 71% |

Example 8

Passenger Car Tire Applications

A high carbon nanotube master batch was used to make a carbon black-filled passenger tread formulation based on SSBR. The composition is set forth in Table 4:

TABLE 4

Composition Example 8

| Component | Control | High Carbon nanotube |
|---|---|---|
| Buna VSL 5025-0 HM SBR 50% Vinyl/15% Styrene | 75.0 | 47.7 |
| Budene 1208 BR high cis | 25 | 25 |
| N330 Carbon Black | 50 | 50 |
| Discrete carbon nanotubes (9 wt.-% of masterbatch) |  | 30 |
| Sundex 790 aromatic oil | 10 | 10 |
| Zinc oxide | 3 | 3 |
| Stearic oxide | 2 | 2 |
| 7240 Wax | 3 | 3 |
| 6PPD Antioxidant | 1 | 1 |
| Sulfur | 2 | 2 |
| Accelerator (TBBS) | 1.25 | 1.25 |
| Co-Accelerator (DPG) | 0.3 | 0.3 |
| Final [phr] | 172.8 | 175.5 |

The components were compounded in a 1.2-1 Banbury lab mixer (Farrel F270) whereby the temperature in the first pass was 65° C. and in the final pass 50° C. After the final pass, the test pieces are formed and cured.

The properties are summarised in Table 5 below:

TABLE 5

Results Example 8

|  | Comparative | Invention |
|---|---|---|
| E' Storage Modulus at −20° C. Winter traction (lower is better) | 1.28E+8 | 8.57E+7 |

TABLE 5-continued

Results Example 8

|  | Comparative | Invention |
|---|---|---|
| E' Storage Modulus at 30° C. Dry handling (higher is better) | 1.33E+7 | 2.02E+7 |
| Tan Delta at 30° C. Rolling resistance (lower is better) | 0.109 | 0.106 |

Example 9

Truck Tire Application

In a similar manner as in Example 8, a HCF-ESBR masterbatch was used for making an off-road truck tread (OTR) formulation. The following components were compounded in a 1.2-1 Banbury lab mixer (Farrel F270):

TABLE 6

Composition Example 9

|  | Comparative | Invention |
|---|---|---|
| Natural rubber (CV60) | 73.3 | 73.3 |
| Discrete Carbon Nanotube Masterbatch |  | 26.7 |
| Styron Brand ESBR (1502) | 26.7 |  |
| Commercial Grade Carbon Black (N220) | 35 | 35 |
| Silica 7000GR | 15 | 15 |
| Tudalen 4192 TDAE Oil | 3 | 3 |
| Anti-oxidant (6PPD) | 2 | 2 |
| UV Protection - Antilux 654 | 2 | 2 |
| Stearic acid | 2 | 2 |
| Zinc oxide | 4 | 4 |
| Sulfur | 1.5 | 1.5 |
| Accelerator (CBS) | 1.4 | 1.4 |
| Final [phr] | 1.4 | 1.4 |

Figure 5:
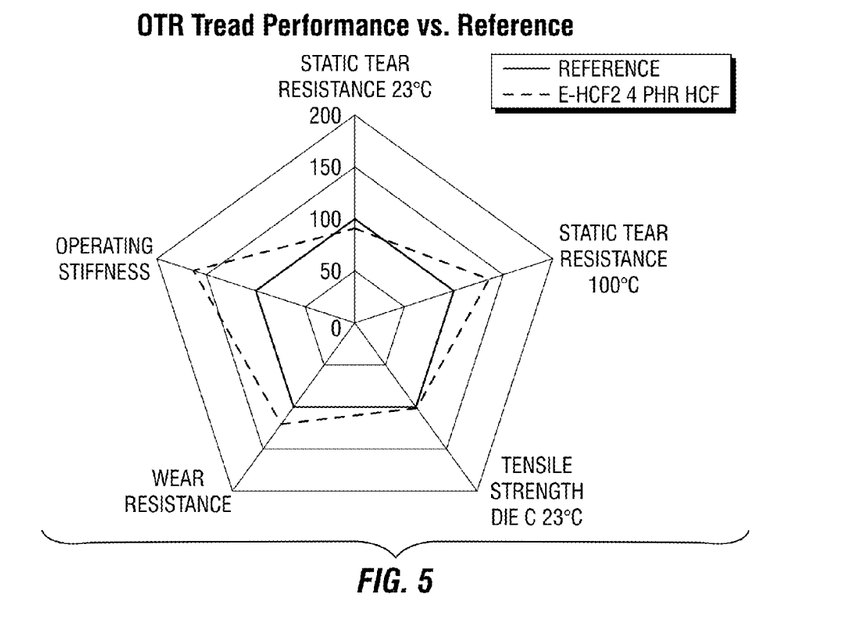
FIG. 5 is a comparison that shows off road truck tread performance for a reference formulation and an HCF formulation.
Figure 6:
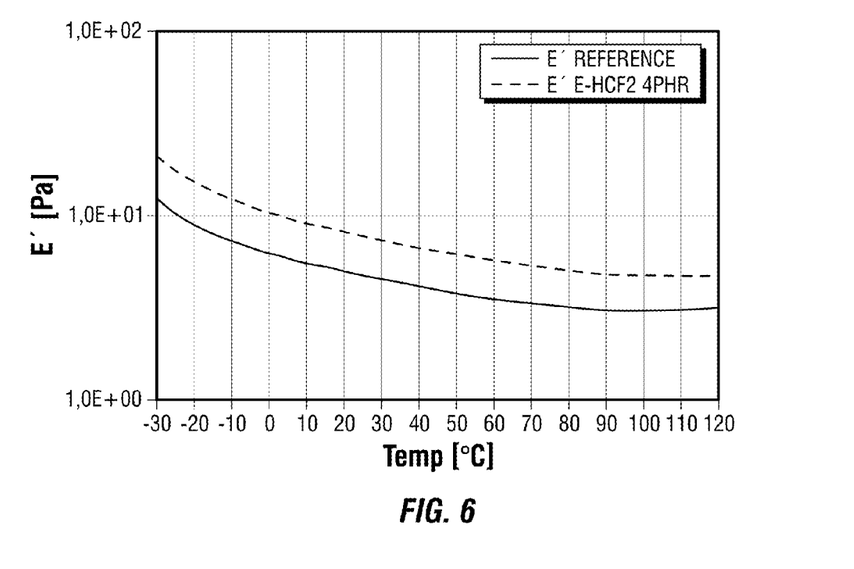
FIG. 6 is a comparison that shows off road truck tread performance for a reference formulation and an HCF formulation.

Results are shown in FIGS. 5 and 6

Example 10

HCF-ESBR Master Batch in Truck Tread Formulation

As in Examples 8 and 9 above, a truck tire tread was made from the following components:

TABLE 7

Composition Example 10

|  | Comparative | Invention |
|---|---|---|
| CV60 | 73.3 | 73.3 |
| Discrete Carbon Nanotubes Masterbatch (E-HCF2) |  | 26.7 |
| Styron ESBR (1502) | 26.7 |  |
| Commercial Grade Carbon Black (N110) | 50 | 50 |
| Tudalen 4192 TDAE Oil | 10 | 10 |
| Anti-oxidant (6PPD) | 2 | 2 |
| Antilux 654 | 2 | 2 |
| Stearic acid | 3 | 3 |
| Zinc oxide | 3 | 3 |
| Sulfur | 1.5 | 1.5 |
| Accelerator (TBBS) | 1.3 | 1.3 |
| Final [phr] | 172.8 | 172.8 |

Figure 7:
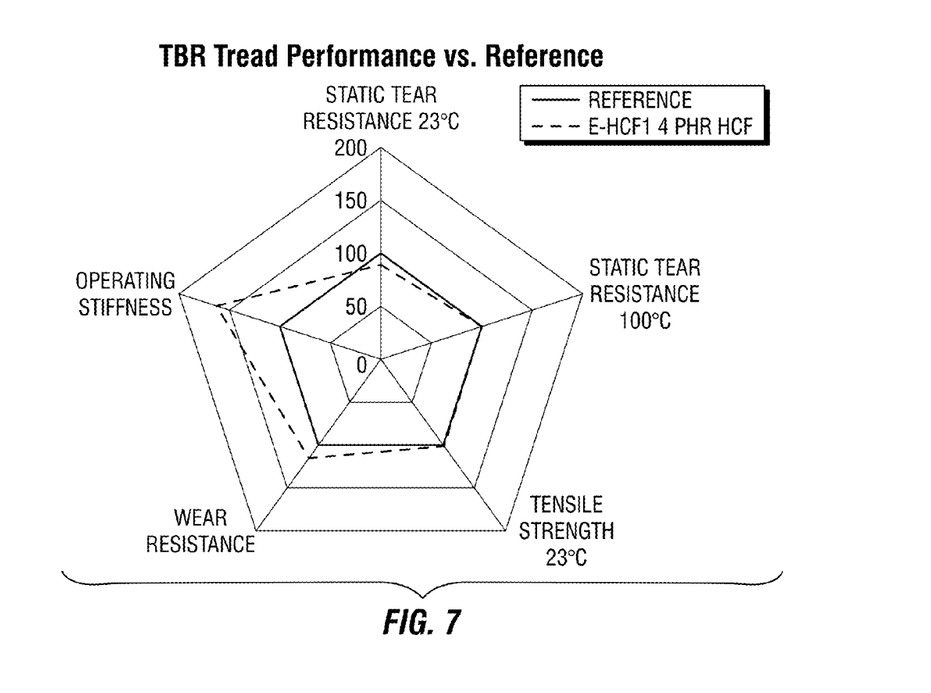
FIG. 7 is a comparison that shows truck tread performance for a reference formulation and an HCF formulation.
Figure 8:
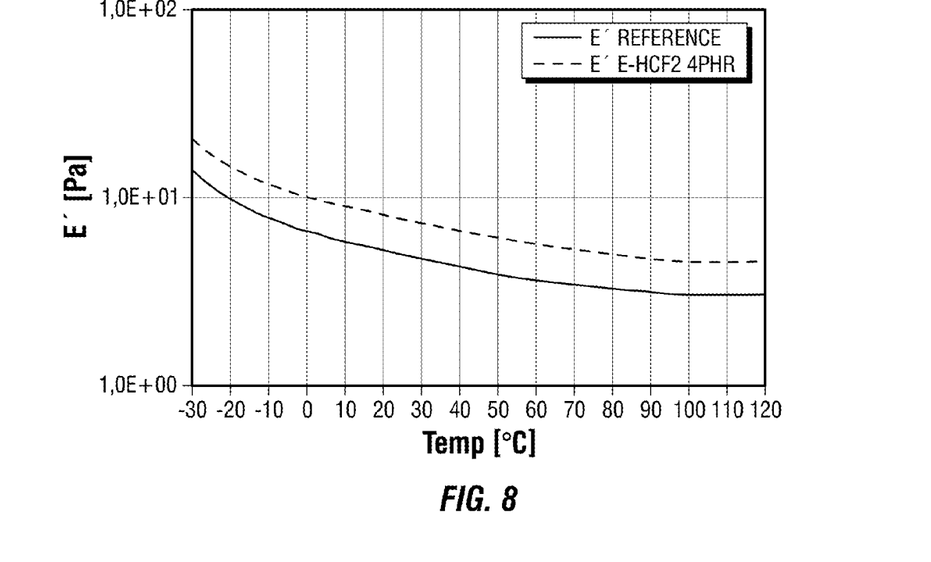
FIG. 8 is a comparison that shows truck tread performance for a reference formulation and an HCF formulation.

The results are shown in FIGS. 7 and 8.

EMBODIMENTS

The following embodiments emphasise certain aspects of the present invention.

1. A composition comprising a plurality of discrete carbon nanotube fibers having an aspect ratio of from about 25 to about 500, and at least one natural or synthetic elastomer, and optionally at least one filler.

2. The composition of embodiment 1 wherein at least 70 percent, preferably at least 80 percent, by weight of the nanotube fibers are fully exfoliated.

3. The composition of embodiments 1 or 2 wherein the nanotube fibers are further functionalized.

4. The composition of embodiments 1 to 3, wherein the carbon nanotube fibers comprise an oxidation level from about 3 weight percent to about 15 weight percent.

5. The composition of embodiments 1 to 4, wherein the carbon nanotube fibers comprise from about 1 weight percent to about 30 weight percent of the composition.

6. The composition of embodiments 1 to 5, in the form of free flowing particles.

7. The composition of embodiments 1 to 6 further comprising at least one surfactant or dispersing aid.

8. The composition of embodiments 1 to 7, wherein the natural or synthetic elastomer is selected from the group consisting of natural rubbers, polyisobutylene, polybutadiene and styrene-butadiene, butyl rubber, polyisoprene, ethylene propylene diene rubbers and hydrogenated and non-hydrogenated nitrile rubbers, polyurethanes, polyethers, silicones, halogen modified elastomers, especially chloroprene and fluoroelastomers and combinations thereof.

9. The composition of embodiments 1 to 8, wherein the fibers are not entangled as a mass.

10. A process to form a carbon nanotube fiber/elastomer composite comprising the steps of:
(a) selecting discrete carbon nanotube fibers having an aspect ratio of from 25 to 500,
(b) blending the fibers with a liquid to form a liquid/fiber mixture,
(c) optionally adjusting the pH to a desired level,
(d) agitating the mixture to a degree sufficient to disperse the fibers to form a dispersed fiber mixture,
(e) optionally combining the dispersed fiber mixture with at least one surfactant,
(f) combining the dispersed fiber mixture with at least one elastomer at a temperature sufficient to incorporate the dispersed fiber mixture to form a carbon nanotube fiber/elastomer composite/liquid mixture,
(g) isolating the resulting carbon nanotube fiber/elastomer composite from the liquid.

11. The process of embodiment 10 wherein the carbon nanotube fibers comprise from about 1 to about 30 weight percent of the fiber/elastomer composite of (g).

12. The process of embodiments 10 or 11, wherein the liquid is aqueous based.

13. The process of embodiments 10 or 12, wherein the agitating step (d) comprises sonication.

14. The process of embodiments 10 or 13, wherein the elastomer is selected from the group consisting of natural rubbers, polyisobutylene, polybutadiene and styrene-butadiene rubber, ethylene propylene diene rubbers, butyl rubber, polyisoprene and hydrogenated and non-hydrogenated nitrile rubbers, polyurethanes, polyethers, halogen containing elastomers and fluoroelastomers and combinations thereof 15. The composition of embodiments 1 to 9 further comprising sufficient natural or synthetic elastomer to form a formulation comprising from about 0.1 to about 25 weight percent carbon nanotube fibers.

16. The composition of embodiments 1 to 9 and 15 in the form of a molded or fabricated article, such as a tire, a hose, a belt, a seal, a wiper blade, an anti-vibration part, and a tank track.

17. The composition of embodiments 1 to 9 and 15 to 16 further comprising carbon black and/or silica and wherein a molded film comprising the composition has a tensile modulus at 5% strain and 25 degrees C. of at least about 12 MPa.

18. The composition of embodiments 1 to 9 and 15 to 17 further comprising carbon black and/or silica, and wherein a molded film comprising the composition has a tear property at 25 degrees C. of at least about 0.8 MPa.

19. The composition of embodiments 1 to 9 and 15 to 18 further comprising filler, and wherein a moulded film comprising the composition has a tensile modulus at 5% strain and 25 degrees C. of at least about 8 MPa.

20. A carbon nanotube fiber/elastomer composite, wherein the carbon nanotube fibers are discrete fibers and comprise from about 10 to about 20 weight percent fibers and wherein the elastomer comprises a styrene copolymer rubber.

21. A method for obtaining individually dispersed carbon nanotubes in rubbers and/or elastomers comprising
(a) forming a solution of exfoliated carbon nanotubes at pH greater than or equal to about 7,
(b) adding the solution to a rubber or elastomer latex to form a mixture at pH greater than or equal to about 7,
(c) coagulating the mixture to form a concentrate,
(d) optionally incorporating other fillers into the concentrate, and
(e) melt-mixing said concentrate into rubbers and/or elastomers to form elastomeric composites.

22. The method of embodiment 21 wherein the carbon nanotubes comprise less than or equal to about 2% wt of the solution.

23. The method of embodiments 21 and 22, wherein the coagulation step (c) comprises mixing with organic molecules of high water solubility such as acetone, denatured alcohol, ethyl alcohol, methanol, acetic acid, tetrahydrofuran that partially or wholly removes surfactants form the latex/carbon nanotube fiber concentrate.

24. The method of embodiments 21 to 23, wherein the coagulation step (c) comprises drying, steam stripping or mechanical agitation of the mixture to fully retain surfactants from the latex/carbon nanotube fiber concentrate.

25. The method of embodiments 21 to 24, wherein the coagulation step (c) comprises adding a polymeric coagulating agent, preferably polyethylene oxide.

26. The method of embodiments 21 to 25, wherein the coagulation step (c) comprises adding at least one acid to the mixture at pH less than or equal to about 4.5 together with at least one monovalent inorganic salt to retain surfactants from the latex/carbon nanotube fiber concentrate.

27. The method of embodiments 21 to 26, wherein the mixture or concentrate has a divalent or multivalent metal ion content of less than about 20,000 parts per million.

28. The method of embodiments 21 to 27, wherein the mixture or concentrate has a divalent or multivalent metal ion content of less than about 10,000 parts per million.

29. The method of embodiments 21 to 28, wherein the mixture or concentrate has a divalent or multivalent metal ion content of less than about 1,000 parts per million.

30. The method of embodiments 21 to 29, wherein the coagulation step (c) is such that agglomerations of carbon nanotubes comprise less than 1 percent by weight of the concentrate and wherein the carbon nanotube agglomerates comprise more than 10 microns in diameter.

31. An individually dispersed carbon nanotube/rubber or carbon nanotube/elastomer concentrate comprising free flowing particles wherein the concentrate contains a concentration of less than 20,000 parts per million divalent or multivalent metal salt.

32. An individually dispersed carbon nanotube/rubber or carbon nanotube/elastomer concentrate comprising free flowing particles wherein the concentrate contains agglomerations of carbon nanotubes that comprise less than 1 percent by weight of the concentrate and wherein the carbon nanotube agglomerates comprise more than 10 micrometers in diameter.

33. A composite comprising the concentrate of embodiments 31 or 32.

34. A method of dispersing the individually dispersed carbon nanotube/rubber or carbon nanotube/elastomer concentrate into an elastomer by first melt mixing the elastomer and concentrate to a uniform consistency before addition of other fillers and oils.

35. The composition of embodiment 5 comprising a mixture of natural and synthetic elastomers such that each elastomer is compatible with at least one of the elastomers such that the nanotubes are individually dispersed in the mixture of elastomer(s).

36. The composition of embodiment 35 wherein at least one of the elastomers does not comprise nanotubes.

37. A composition comprising one first elastomer and nanotubes, another different second elastomer and nanotubes, and yet another third elastomer which does not comprise nanotubes.

38. A process to increase cure rate of a composition comprising at least one natural or synthetic elastomer and carbon nanotubes, comprising selecting discrete carbon nanotubes to form the cured composition, wherein the cured composition has at least a 25 percent curing rate increase over the curing rate obtained for a cured elastomer not comprising carbon nanotubes.

39. A composition of (A) elastomers, fillers and discrete carbon nanotubes wherein to maintain or increase stiffness or hardness as compared to (B) a composition not containing discrete carbon nanotubes, wherein composition (A) has less filler content than (B).

40. A composition of embodiment 39 wherein 1× parts per hundred elastomer discrete carbon nanotube of composition (A) replaces 5× parts per hundred elastomer or more of the non-carbon nanotube filler of composition (B), where x is 0.1-15. 17.

41. A method of mixing carbon nanotubes and at least one first elastomer, wherein a master batch of carbon nanotubes is first melt mixed with the elastomer, either the same or different from the first elastomer, at a temperature from about 20 to about 200° C. subsequently then additional elastomers, fillers, and additives are added and melt mixed further, to produce a composition suitable for vulcanization.

42. A method of mixing carbon nanotubes and at least one first elastomer, wherein a master batch of carbon nanotubes is first mixed with the elastomer, either the same or different from the first elastomer, at a temperature from about 20 to about 200° C. and in the presence of at least one solvent, then the at least one solvent is removed, subsequently and optionally additional elastomers, fillers and additives are added and mixed further to produce a composition suitable for vulcanization.

43. A method of mixing carbon nanotubes and at least one first elastomer, wherein a master batch of carbon nanotubes is first mixed with the elastomer, either the same or different from the first elastomer, at a temperature from about 20 to about 200° C. and in the presence of at least one solvent, subsequently and optionally additional elastomers, fillers and additives are added and mixed further, followed by solvent removal to produce a composition suitable for vulcanization.

The invention claimed is:

1. A composition comprising a cured elastomer containing discrete carbon nanotubes, wherein the discrete carbon nanotubes have an aspect ratio of 10 or more, are double wall or multiwall, are present in the range of 0.1 to 30% by weight based on the total weight, and are functionalized.

2. A composition according to claim 1, wherein the cured elastomer is cured by free radical or ionization agents.

3. A composition according to claim 2, wherein the cured elastomer is vulcanized during fabrication and/or form fixing.

4. An article made from a composition according to claim 1.

5. An article according to claim 4, which is selected from a tire, a gum chafer, a tire sidewall, a tire tread or casing, a hose, a belt, a seal, an automotive anti-vibration part, a windshield wiper blade, and a tank track pad, wheel, bushings or backer plate components.

6. An article according to claim 5, which is a tire for off-road and passenger car applications, which tire contains rubber and reinforcing fillers including carbon black and/or silica.

7. A method for adjusting the wear resistance, the strength and/or the stiffness of elastomeric articles comprising providing a composition according to claim 1.

8. A method for adjusting the wear resistance, the strength and/or the stiffness of a tire or part thereof including a gum chafer, a tire sidewall, a tire tread or casing, the method comprising providing a composition according to claim 1.

9. The method according to claim 8, wherein the tire tread has a concentration of discrete carbon nanotubes in the range of 0.7 vol. % and 30 vol. % and a concentration of reinforcing filler in the range of 0 to 30 vol. %.

10. The composition of claim 1 wherein the discrete carbon nanotubes are functionalized on the nanotube ends, sidewalls, or both.

11. The composition of claim 1 wherein the discrete carbon nanotubes are functionalized via covalent bonding, ionic bonding, chemisorption, intercalation, surfactant interactions, polymer wrapping, cutting, solvation, or a combination thereof.

12. The composition of claim 1 wherein the discrete carbon nanotubes are functionalized before being separated.

13. The composition of claim 1 wherein the discrete carbon nanotubes are functionalized during separation.

14. The composition of claim 1 wherein the discrete carbon nanotubes are functionalized after being separated.

\* \* \* \* \*

UNITED STATES PATENT AND TRADEMARK OFFICE
CERTIFICATE OF CORRECTION

| | | |
|---|---|---|
| PATENT NO. | : 9,212,273 B2 | |
| APPLICATION NO. | : 13/993206 | |
| DATED | : December 15, 2015 | |
| INVENTOR(S) | : Clive P. Bosnyak et al. | |

It is certified that error appears in the above-identified patent and that said Letters Patent is hereby corrected as shown below:

Claims

In Column 17, Line 19, claim 5, please change -- fire, a gum chafer, a tire -- to
-- tire, a gum chafer, a tire --

Signed and Sealed this
Twenty-eighth Day of June, 2016

Michelle K. Lee
*Director of the United States Patent and Trademark Office*